(12) United States Patent
Abe et al.

(10) Patent No.: US 11,376,078 B2
(45) Date of Patent: Jul. 5, 2022

(54) SURGERY ASSISTANCE SYSTEM

(71) Applicant: LEXI Co., Ltd., Toshima-ku (JP)

(72) Inventors: Yuichiro Abe, Eniwa (JP); Akio Seitoku, Toshima-ku (JP)

(73) Assignee: LEXI Co., Ltd., Toshima-ku (JP)

( * ) Notice: Subject to any disclaimer, the term of this patent is extended or adjusted under 35 U.S.C. 154(b) by 537 days.

(21) Appl. No.: 16/344,718

(22) PCT Filed: Oct. 25, 2016

(86) PCT No.: PCT/JP2016/081600
§ 371 (c)(1),
(2) Date: Apr. 24, 2019

(87) PCT Pub. No.: WO2018/078723
PCT Pub. Date: May 3, 2018

(65) Prior Publication Data
US 2019/0328463 A1 Oct. 31, 2019

(51) Int. Cl.
*A61B 34/20* (2016.01)
*A61B 90/00* (2016.01)

(52) U.S. Cl.
CPC .............. *A61B 34/20* (2016.02); *A61B 90/37* (2016.02); *A61B 90/361* (2016.02); *A61B 2034/2055* (2016.02); *A61B 2034/2065* (2016.02); *A61B 2090/365* (2016.02)

(58) Field of Classification Search
CPC ........ A61B 2034/105; A61B 2034/108; A61B 2034/2055; A61B 2034/2065; A61B 2090/365; A61B 2090/3983; A61B 34/10; A61B 34/20; A61B 90/361; A61B 90/37
See application file for complete search history.

(56) References Cited

U.S. PATENT DOCUMENTS

| | | |
|---|---|---|
| 10,594,998 B1 | 3/2020 | Casas |
| 2002/0077540 A1 | 6/2002 | Kienzle, III |

(Continued)

FOREIGN PATENT DOCUMENTS

| | | |
|---|---|---|
| JP | 2006-130315 A | 5/2006 |
| JP | 2009-82444 A | 4/2009 |

(Continued)

OTHER PUBLICATIONS

Combined Chinese Office Action and Search Report dated Jan. 7, 2021 in Chinese Patent Application No. 201680090405.6 (with English translation), 17 pages.

(Continued)

*Primary Examiner* — Amelie R Davis
(74) *Attorney, Agent, or Firm* — Oblon, McClelland, Maier & Neustadt, L.L.P.

(57) ABSTRACT

A surgery assistance system including: a physically suitable jig to be attached to a predetermined attached portion of a body on which surgery is to be performed; and a surgery assistance device which displays an augmented reality image. The physical suitable jig includes: a site fitting unit that can be fitted with the predetermined attached portion; and an image-recognizing unit including features that can be image-recognized to display the augmented reality image with the surgery assistance device.

16 Claims, 6 Drawing Sheets

(56) References Cited

U.S. PATENT DOCUMENTS

| | | | |
|---|---|---|---|
| 2008/0269596 A1* | 10/2008 | Revie | A61F 2/4603 600/424 |
| 2008/0319491 A1 | 12/2008 | Schoenefeld | |
| 2009/0177081 A1 | 7/2009 | Joskowicz et al. | |
| 2014/0180430 A1* | 6/2014 | Gillman | A61F 2/34 623/22.21 |
| 2015/0220682 A1* | 8/2015 | Netravali | G16B 5/00 703/11 |
| 2015/0327947 A1 | 11/2015 | Schoenefeld | |
| 2016/0143699 A1 | 5/2016 | Tanji | |
| 2016/0191887 A1 | 6/2016 | Casas | |
| 2016/0206379 A1 | 7/2016 | Flett et al. | |
| 2016/0287337 A1 | 10/2016 | Aram et al. | |
| 2018/0008351 A1 | 1/2018 | Schoenefeld | |
| 2018/0071032 A1 | 3/2018 | De Almeida Barreto | |
| 2018/0262743 A1 | 9/2018 | Casas | |
| 2019/0053852 A1 | 2/2019 | Schoenefeld | |
| 2019/0149797 A1 | 5/2019 | Casas | |
| 2019/0246088 A1 | 8/2019 | Casas | |
| 2019/0349559 A1 | 11/2019 | Casas | |
| 2020/0053335 A1 | 2/2020 | Casas | |

FOREIGN PATENT DOCUMENTS

| | | |
|---|---|---|
| WO | WO 2006/075331 A2 | 7/2006 |
| WO | WO 2014/200016 A1 | 12/2014 |
| WO | WO 2016/154557 A1 | 9/2016 |

OTHER PUBLICATIONS

International Search Report dated Dec. 13, 2016 in PCT/JP2016/081600 filed on Oct. 25, 2016.

Office Action issued Sep. 6, 2021 in corresponding Chinese Patent Application No. 201680090405.6 (with English Translation), 9 pages.

Notice of Reasons for Refusal dated Jul. 28, 2020 in Japanese Patent Application No. 2018-546971 (with English machine translation), 8 pages.

Extended European Search Report dated Apr. 17, 2020 in European Patent Application No. 16920226.4, 8 pages.

Office Action dated Jan. 25, 2022, in Chinese Patent Application No. 201680090405.6 w/English Machine Transiation.

* cited by examiner

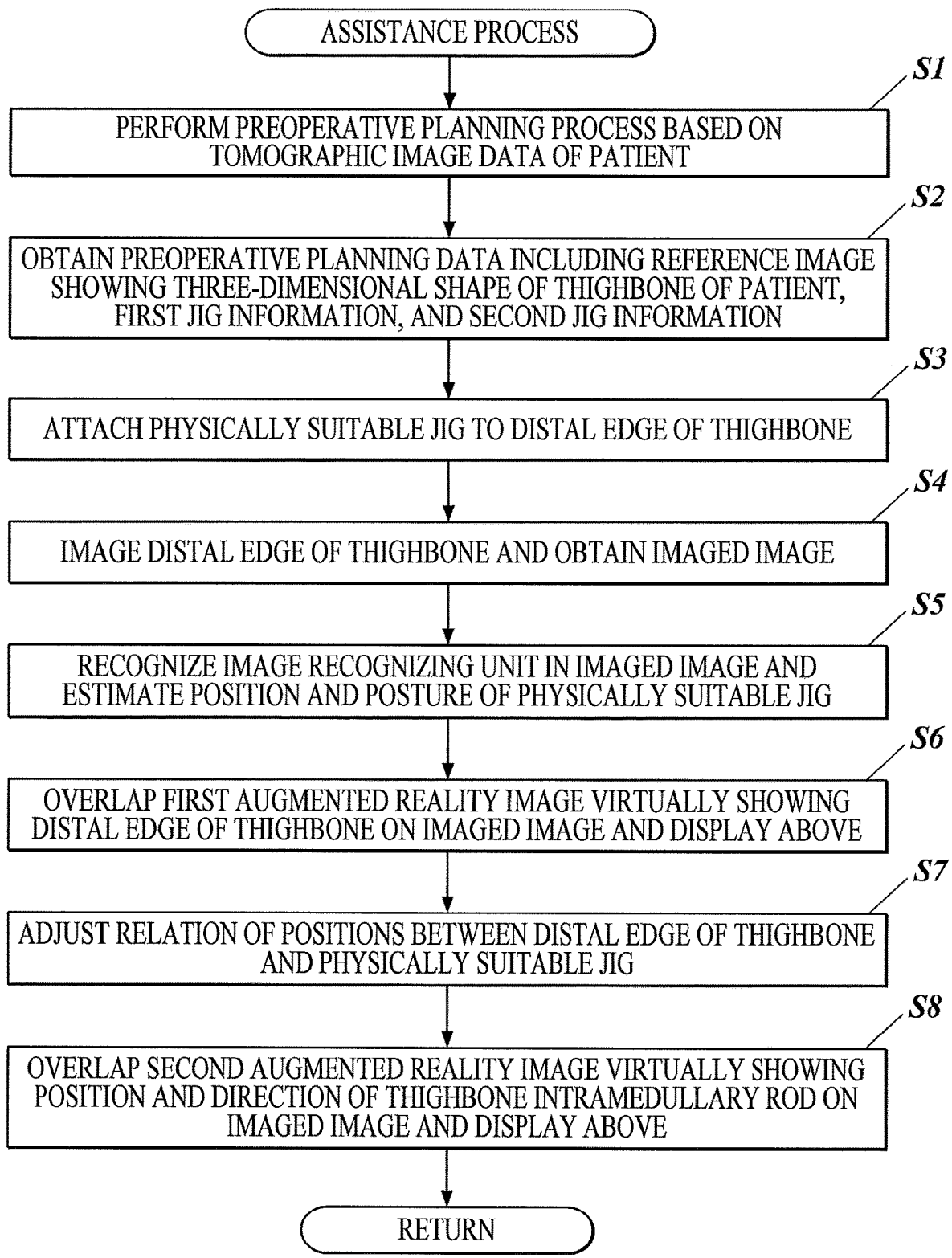

SURGERY ASSISTANCE SYSTEM

TECHNICAL FIELD

The present invention relates to a surgery assistance system which supports a surgery, more specifically, orthopedic surgery such as attaching an implant inside a patient's body.

BACKGROUND ART

Conventionally, there are surgeries to attach and fuse a spinal cage or artificial vertebral centrum to fix, correct and stabilize a spine and replacement surgery to replace a knee joint or a hip joint with a metallic or ceramic artificial joint.

In surgeries as described above, a medical tomographic image of a site where an implant of the patient is planned to be attached is used in advance in preoperative planning to simulate the shape and size of the implant to be attached and the position and the angle that the implant is attached (for example, see Patent Literature 1). Moreover, in order to attach the implant according to the preoperative plan, there is a well-known method to use a navigation system or various guiding jigs (for example, see Patent Literature 2).

PRIOR ART DOCUMENT

Patent Literature

Patent Literature 1: Japanese Patent Application Laid-Open Publication No. 2009-82444
Patent Literature 2: Japanese Patent Application Laid-Open Publication No. 2006-130315

DISCLOSURE OF THE INVENTION

Problems to be Solved by the Invention

Navigation systems are expensive and the apparatus itself is large, and therefore the percentage of coverage is not high. Guiding jigs can be introduced with comparatively low costs. However, the guiding jig needs to be attached accurately in a predetermined position of the bone in order to accurately attach the implant or to perform osteotomy. There is a physically suitable guiding jig including a surface shape corresponding to the shape of the bone of the patient to be fit to the bone in order to enhance the accuracy of attaching the guiding jig. However, the accuracy of attaching decreases when the surface of the bone is smooth and the number of characteristic uneven portions are small.

That is, even physically suitable guiding jigs may cause reduction of accuracy in attaching implants if the attaching accuracy of the guiding jigs reduces. Therefore, there is a demand for a method to confirm whether the guiding jig itself is accurately attached to a predetermined position in the bone.

When a minimally invasive surgery is performed to minimize the invasiveness to the body in surgical operation, the width that the skin is cut open is relatively small. Therefore, there is a problem that the guiding jig may have a size that cannot be attached to the predetermined position of the bone.

The present invention is invented in view of the above problems, and the purpose of the present invention is to enhance accuracy of attaching a physically suitable jig and to provide a small physically suitable jig which can be applied to minimally invasive surgery.

Means for Solving the Problem

According to an aspect of the present invention, there is a surgery assistance system including: a physically suitable jig attached to a predetermined attached portion of a body on which surgery is performed; and a surgery assistance apparatus which displays an augmented reality image to support the surgery, wherein, the physically suitable jig includes, a site fitting unit which can be fitted in the predetermined attached portion, and an image recognizing unit which includes a feature which can be image-recognized to display an augmented reality image with the surgery assistance apparatus, the surgery assistance apparatus includes, a first obtainer which obtains a reference image regarding a three-dimensional shape of the predetermined attached portion of the body and a treated portion on which the surgery is performed, and first jig information including an attaching position of the physically suitable jig on a three-dimensional model based on the reference image, a second obtainer which obtains an imaged image in which the physically suitable jig is attached to the predetermined attached portion and the treated portion is imaged, an estimating unit which recognizes the image recognizing unit of the physically suitable jig in the imaged image obtained by the second obtainer, and which estimates a position and posture of the physically suitable jig in the imaged image, and a display controller which, based on the reference image and the first jig information obtained by the first obtainer, overlaps on the imaged image a first augmented reality image virtually showing the treated portion in a position and a posture corresponding to the position and the posture of the physically suitable jig in the imaged image estimated by the estimating unit and displays the above on the display.

Advantageous Effect of the Invention

According to the present invention, it is possible to enhance accuracy of attaching a physically suitable jig and to provide a small physically suitable jig which can be applied to minimally invasive surgery.

BRIEF DESCRIPTION OF THE DRAWINGS

FIG. 4 is a flowchart showing an example of an operation regarding an assistance process in the surgery assistance system shown in FIG. 1.

EMBODIMENT FOR CARRYING OUT THE INVENTION

The specific details of the present invention are described with reference to the drawings. The scope of the present invention is not limited to the illustrated examples.

The surgery assistance system 100 according to an embodiment applying the present invention is described with reference to FIG. 1 to FIG. 5C.

Figure 1:
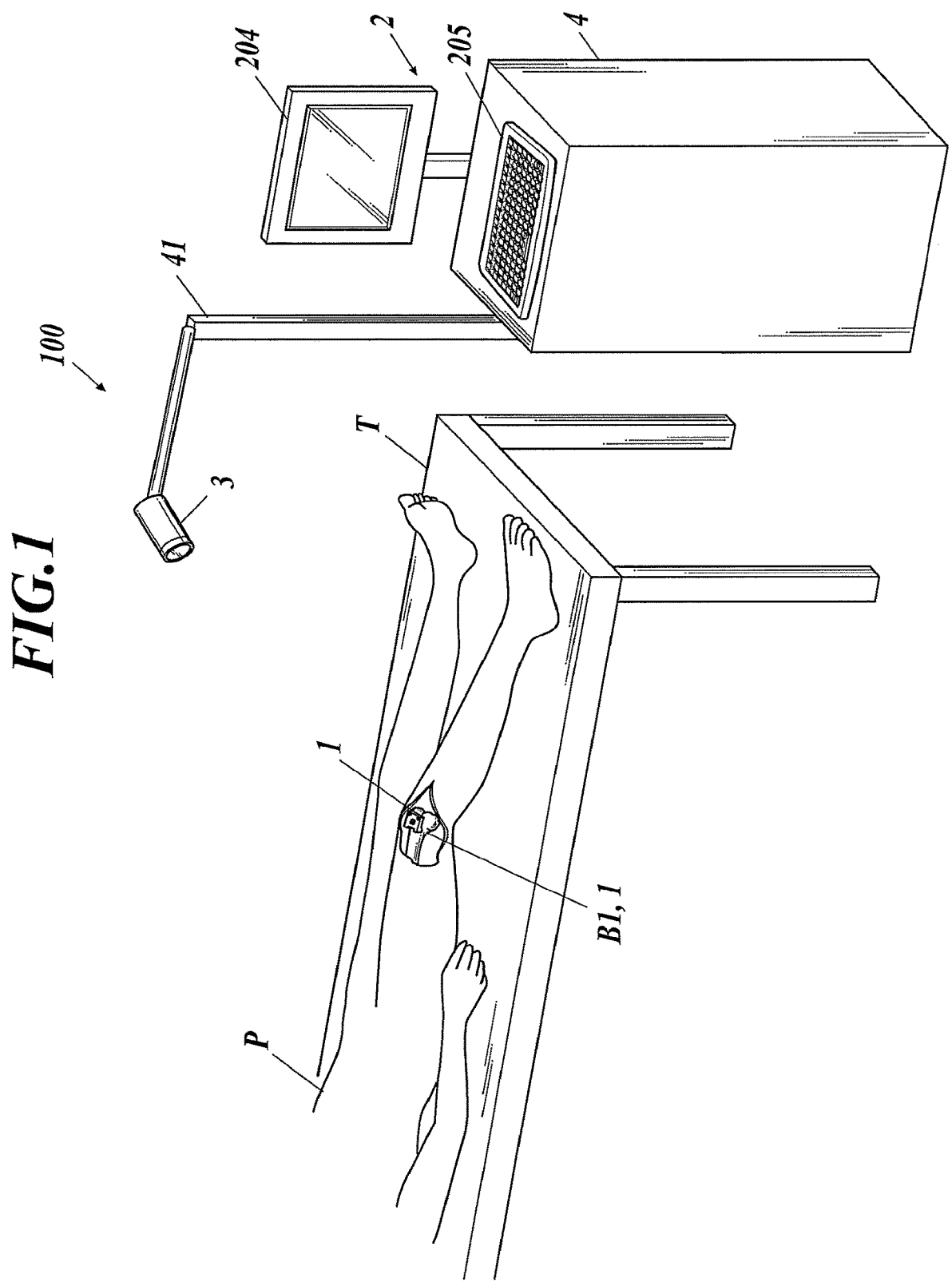
FIG. 1 is a perspective view to describe a schematic configuration of a surgery assistance system according to an embodiment applying the present invention.

FIG. 1 is a perspective view describing a schematic configuration of the surgery assistance system 100.

As shown in FIG. 1, the surgery assistance system 100 according to the present embodiment is, for example, a system used in an artificial knee joint replacement surgery. Specifically, the surgery assistance system 100 includes a physically suitable jig 1 which is attached to a body of the patient P, and a surgery assistance apparatus 2 which performs intraoperative assistance during the surgery.

According to the present embodiment, the artificial knee joint replacement surgery is one example of the surgery that is performed, but the present invention is not limited to the above. The surgery that employs the surgery assistance system 100 can be suitably changed to, for example, surgery which attaches and fixes a spinal cage or an artificial vertebral centrum to fix, correct, and stabilize the spine or artificial hip joint replacement surgery.

FIG. 1 shows a state in which a patient P is not fixed on an operating table T, but the patient P may be fixed so that the physician is able to easily perform the surgery.

<Physically Suitable Jig>

Figure 2A:
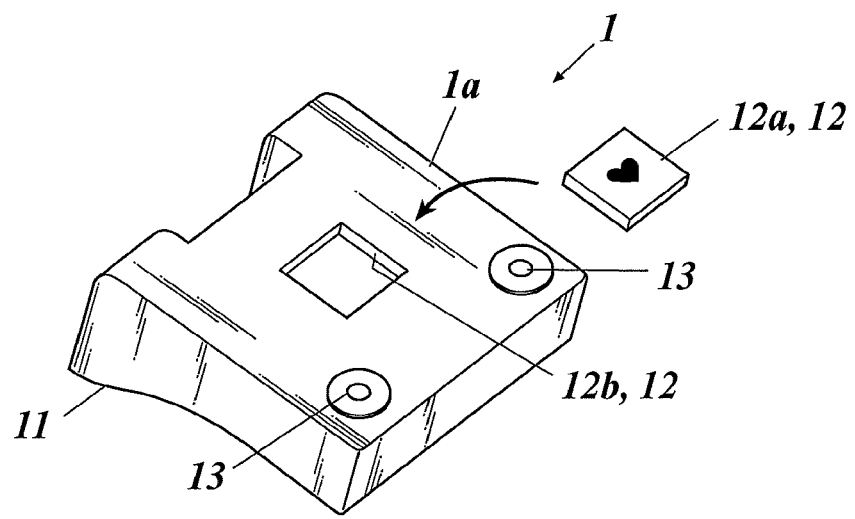
FIG. 2A is a perspective view showing a physically suitable jig included in a surgery assistance system shown in FIG. 1.

First, the physically suitable jig 1 is described in detail with reference to FIG. 2A and FIG. 2B. FIG. 2A is a perspective view showing a physically suitable jig 1.

For example, the physically suitable jig 1 is attached to a bone (predetermined attached portion) of a body of the patient P on which surgery such as artificial knee joint replacement is performed (see FIG. 1). Here, physically suitable means that it is formed to match a shape of a bone B unique for each patient P and it has a contact surface with a surface shape in a relation complementary to the uneven shape of the surface of the bone B (for example, distal edge of thighbone B1). That is, the physically suitable jig 1 can be fit to a predetermined attached portion of the bone B in the patient P.

Specifically, as shown in FIG. 2A, in the physically suitable jig 1, a site fitting unit 11 which can be fit in a predetermined position of the distal edge of the thighbone B1, and an image recognizing unit 12 provided with a marker 12a for displaying an augmented reality image (see FIG. 5B) with the surgery assistance apparatus 2 are formed in a main body unit 1a.

Here, for example, the main body unit 1a is formed to extend to the pelvis (not illustrated) side from the distal edge of the thighbone B1, but this is merely one example. The shape of the main body unit 1a is not limited to the above and may be changed to any shape.

The site fitting unit 11 is formed on the surface on the thighbone B1 side in the main body unit 1a, and includes a surface shape with a shape complementary to the uneven shape in the surface of the distal edge of the thighbone B1.

That is, as described later, a preoperative planning process is performed with the surgery assistance apparatus 2 using tomographic image data I. When the attaching position in the distal edge of the thighbone B1 of the physically suitable jig 1 is specified by simulation, for example, a surface shape of the portion fitting unit 11 having a complementary relation with the shape of the attaching position in the distal edge of the thighbone B1 is specified by the Boolean operation process. Then, the main body unit 1a including the site fitting unit 11 with the specified surface shape is formed using a three-dimensional (3D) printer which is not shown. A marker fitting unit 12b (later described) is formed as one with the main body unit 1a to be able to fit the marker 12a in the image recognizing unit 12.

With this, a site fitting unit 11 which can be fit to the attaching position (predetermined attached portion) of the distal edge of the thighbone B1 is formed.

The image recognizing unit 12 includes a feature which can be recognized for displaying the augmented reality image with the surgery assistance apparatus 2. Specifically, the image recognizing unit 12 is provided in a predetermined position of the main body unit 1a (for example, a position in which the site fitting unit 11 is not provided), and the marker 12a is fitted and formed in the marker fitting unit 12b carved from the surface of the predetermined position.

For example, the marker fitting unit 12b is a concave unit with a predetermined depth formed in a substantial rectangle from a planar view. For example, an outer edge portion of the marker 12a has a substantial rectangular shape substantially equal to an outer form of the marker fitting unit 12b, and the size is formed to be slightly smaller than the marker fitting unit 12b. The marker 12a includes a thickness substantially equal to the depth of the concave unit of the marker fitting unit 12b.

With this, the marker 12a is stored in the marker fitting unit 12b and adhered with a predetermined adhering means (for example, adhesive or double-sided tape), and the marker 12a is positioned in each direction, in the front and back direction, in the left and right direction and in the up and down direction.

In the predetermined position on the surface opposite of the base of the marker fitting unit 12b of the marker 12a, a predetermined design (for example, heart) is formed for image recognizing by the surgery assistance apparatus 2.

Figure 2B:
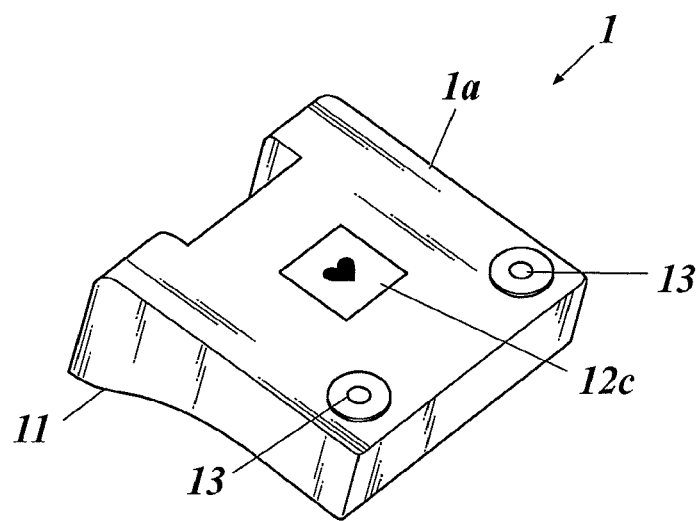
FIG. 2B is a perspective view showing a modification of the physically suitable jig.

For example, as shown in FIG. 2B, the image recognizing unit 12 includes a marker 12c formed as one with the main body unit 1c. The predetermined design (for example, heart) for image recognizing by the surgery assistance apparatus 2 is formed in the marker 12c similar to the marker 12a, and the position, shape, and direction of the predetermined design is the same as the marker 12a.

The marker 12c (image recognizing unit 12) can be formed in the main body unit 1c with the site fitting unit 11 when the main body unit 1c is made using the three-dimensional printer or can be carved by a laser after the main body unit 1c is made.

In the main body unit 1a, two pin inserting holes 13 are formed to insert a pin (not illustrated) used for fixing the physically suitable jig 1 attached to the thighbone B1.

The physically suitable jig 1 is formed from material such as polyamide resin and titanium alloy but the materials above are merely examples and the material is not limited to the above. The material can be suitably and freely changed to any biocompatible material.

<Surgery Assistance Apparatus>

Figure 3:
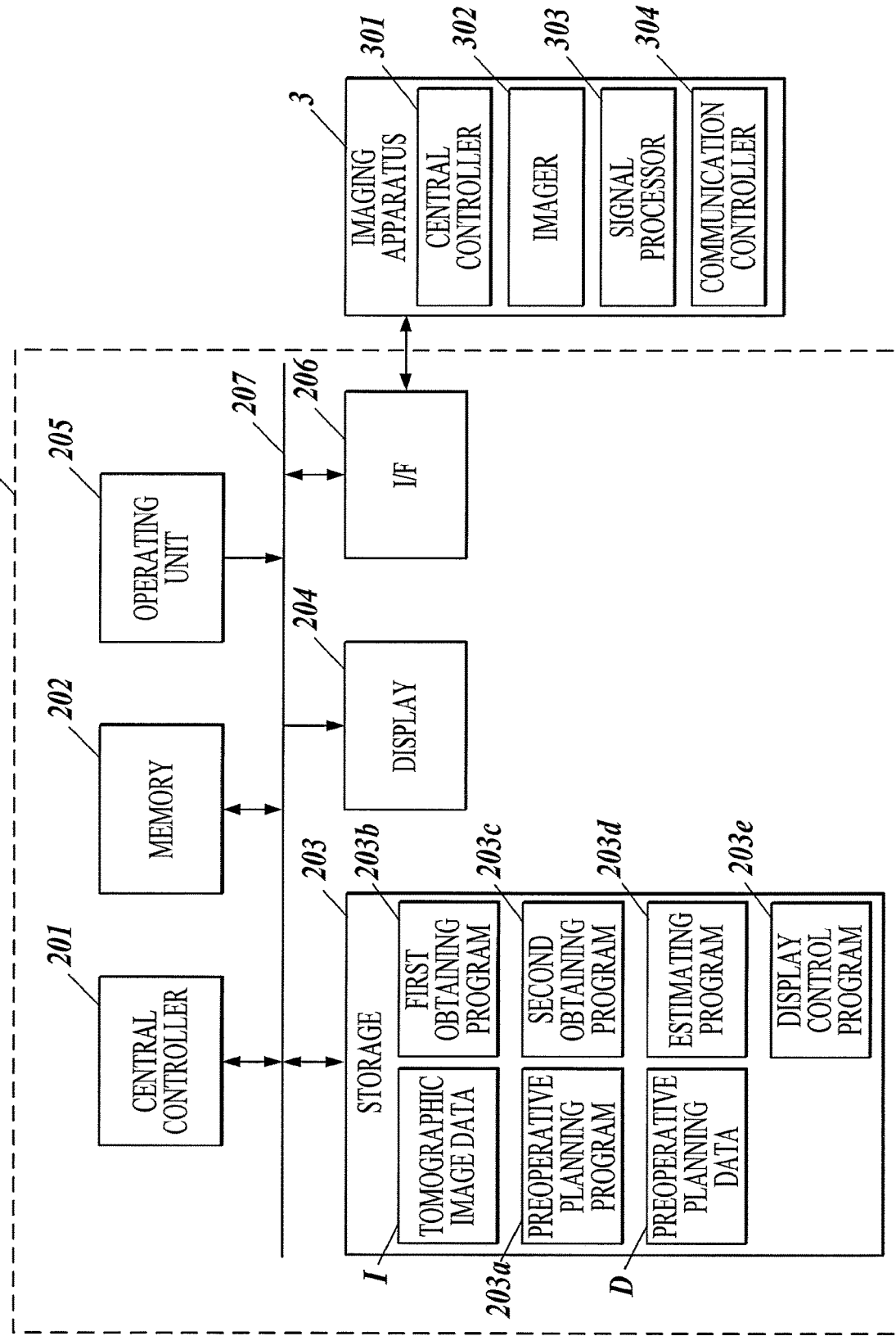
FIG. 3 is a block diagram showing a functional configuration of a surgery assistance apparatus included in the surgery assistance system shown in FIG. 1.

Next, the surgery assistance apparatus 2 is described in detail with reference to FIG. 3. FIG. 3 is a block diagram showing a functional configuration of the surgery assistance apparatus 2.

For example, the surgery assistance apparatus 2 includes a personal computer (PC). An imaging apparatus 3 which images a treated portion (for example, knee joint) of the patient P is connected to the surgery assistance apparatus 2. For example, as shown in FIG. 1, a display 204 and an operating unit 205 (later described) of the surgery assistance apparatus 2 are provided on a base 4. A supporting arm 41 with the imaging apparatus 3 attached to its tip is provided on the base 4. A direction or height imaged when the imaging apparatus 3 performs imaging can be adjusted by the supporting arm 41.

As shown in FIG. 3, the surgery assistance apparatus 2 includes, specifically, a central controller 201, a memory 202, a storage 203, a display 204, an operating unit 205, and an interface (I/F) 206. Each unit of the surgery assistance apparatus 2 is connected to each other through a bus 207.

The central controller 201 controls each unit of the surgery assistance apparatus 2. That is, although illustration is omitted, the central controller 201 includes a CPU (Central Processing Unit). The CPU reads out a specified program from a system program and application programs stored in the storage 203, deploys the program in a work area of the memory 202, and performs various processes according to the program. Here, the CPU of the central controller 201 stores various processing results in the memory 202 and displays the processing results as necessary on the display 204.

For example, the memory 202 includes a DRAM (Dynamic Random Access Memory) and includes a work area which temporarily stores various programs and data read by the CPU of the central controller 201.

The storage 203 is a storage which includes a flash memory, EEPROM (Electrically Erasable Programmable Read Only Memory), HDD (Hard Disk Drive), and the like. The storage 203 is a storage which is able to write and read data and programs.

Specifically, the storage 203 stores tomographic image data I, preoperative planning program 203a, preoperative planning data D, first obtaining program 203b, second obtaining program 203c, estimating program 203d, and display control program 203e.

For example, the tomographic image data I is image data imaged by a medical tomographic image diagnostic apparatus (not shown) such as a X-ray CT (Computed Tomography) apparatus or MRI (Magnetic Resonance Imaging system) apparatus showing a treated portion (for example, a knee joint replaced to an artificial knee joint) on which surgery for the patient P is performed. That is, the tomographic image data I is image data imaged by the medical tomographic image diagnostic apparatus before the artificial knee joint replacement surgery showing a thighbone B1 and a shinbone (not shown) included in the knee joint of the patient P.

The tomographic image data I may be data transmitted to the surgery assistance apparatus 2 from the medical tomographic image diagnostic apparatus through a network such as an in-house LAN, or may be data obtained by the surgery assistance apparatus 2 through a storage medium such as a memory card.

The preoperative planning program 203a is a program to execute functions regarding the preoperative planning process for the artificial knee joint replacement surgery.

That is, the CPU of the central controller 201 reads out the preoperative planning program 203a from the storage 203, and according to the preoperative planning program 203a, specifies by simulation the shape and the dimensions of the artificial knee joint (thighbone member and shinbone member, not shown) to be attached, direction of a thighbone intramedullary rod inserted in the thighbone B1 and position of its inserting point, osteotomy position of the thighbone B1, direction of the shinbone intramedullary rod inserted in the shinbone and position of its inserting point, osteotomy position of the shinbone, and the like.

The preoperative planning process is a well-known technique, and the detailed description is omitted here. For example, the CPU of the central controller 201 generates image data of the reference image showing a three-dimensional shape of the thighbone B1 of the patient P from the tomographic image data I imaged by the medical tomographic image diagnostic apparatus before the artificial knee joint replacement surgery. Here, instead of the tomographic image data I, a three-dimensional shape of the bone B (thighbone B1) can be estimated based on an X-ray image imaged from two directions and image data showing the three-dimensional shape of the bone B can be generated to be used as the reference image.

Then, the CPU of the central controller 201 establishes a coordinate system on a three-dimensional model of the thighbone B1 displayed on the display 204, and the position where the thighbone side member included in the artificial knee joint is planned to be set is simulated and specified. The CPU of the central controller 201 simulates and generates first jig information including a suitable attaching position and attaching direction of the physically suitable jig 1 with relation to the thighbone B1 on the three-dimensional model of the thighbone B1 displayed on the display 204 based on the tomographic image data I. The CPU of the central controller 201 specifies a surface shape of the site fitting unit 11 having a complementary relation with the shape of the attaching position at the distal edge of the thighbone B1 by the Boolean operation process. With reference to the position of the physically suitable jig 1 on the three-dimensional model of the thighbone B1, the CPU of the central controller 201 simulates and generates second jig information including attaching position and attaching direction of various guiding assistance jigs such as the thighbone intramedullary rod inserted in the thighbone B1 to assist guiding of attaching the thighbone side member (implant) to the thighbone B1 and the thighbone osteotomy guiding members (not shown) which guide osteotomy of the thighbone B1 with the thighbone intramedullary rod as the reference. The CPU of the central controller 201, for example, generates various intraoperative assistance parameters such as functional axis, a position of center in a caput of the thighbone B1, valgus/varus angle, bending/extending angle, rotating angle, etc.

The generating of the first jig information and the second jig information can be performed automatically by simulation or the direction and the position of the jig can be finely adjusted based on the predetermined operation on the operating unit 205 by the physician.

Similarly for the shinbone side of the knee joint, the planned position of providing the shinbone side member included in the artificial knee joint, first jig information, and second jig information are simulated and specified, and the detailed description is omitted.

Various information generated by the preoperative planning process is stored in the storage 203 as the preoperative planning data D.

The preoperative planning process can be performed in the apparatus other than the surgery assistance apparatus 2, and for example, the preoperative planning data D can be transmitted to the surgery assistance apparatus 2 through the network such as an in-house LAN, or the preoperative planning data D can be obtained by the surgery assistance apparatus 2 through the storage medium such as the memory card.

The first obtaining program 203b is a program to execute a function regarding a first obtaining process to obtain a reference image and jig information.

That is, the CPU of the central controller 201 reads out the first obtaining program 203b from the storage 203 and performs the first obtaining process according to the first obtaining program 203b. Here, the CPU of the central controller 201 functions as the first obtaining unit in coordination with the first obtaining program 203b.

Specifically, the CPU of the central controller 201 reads out and obtains the preoperative planning data D from the storage 203, and obtains the image data of the reference image showing the three-dimensional shape of the thighbone B1 and the shinbone on which the artificial knee joint of the patient P is planned to be attached. The CPU of the central controller 201 reads out and obtains from the storage 203 the preoperative planning data D, and obtains the first jig information including the attaching position of the physically suitable jig 1 attached to the distal edge of the thighbone B1 on the three-dimensional model of the thighbone B1. The CPU of the central controller 201 reads out and obtains from the storage 203 the preoperative planning data D, and obtains the second jig information including the attaching position and the attaching direction of the thighbone intramedullary rod to assist guiding of attaching the thighbone side member (implant) on the thighbone B1 in the three-dimensional model of the thighbone B1.

Figure 5A:
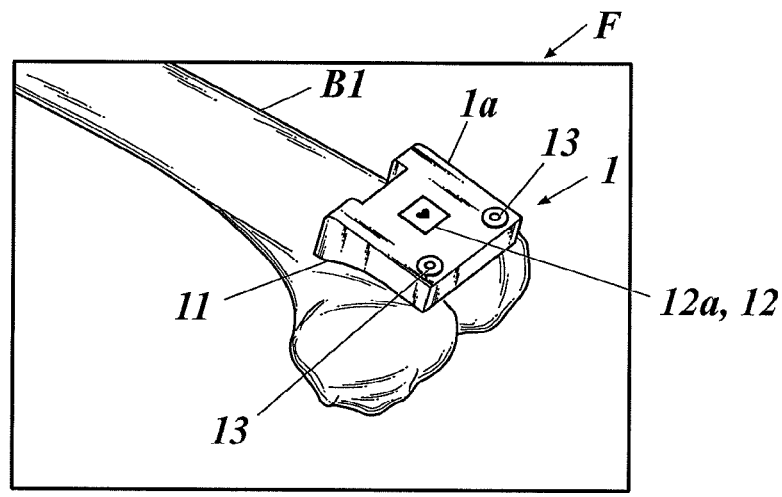
FIG. 5A is a diagram showing an example of an image imaged by an imaging apparatus.

The second obtaining program 203c is a program which executes a function regarding a second obtaining process to sequentially obtain imaged images F (see FIG. 5A).

That is, the CPU of the central controller 201 reads out the second obtaining program 203c from the storage 203 and performs the second obtaining process according to the second obtaining program 203c. Here, the CPU of the central controller 201 functions as a second obtaining unit in coordination with the second obtaining program 203c.

Specifically, the CPU of the central controller 201 obtains the imaged image F imaged by the imaging apparatus 3. The imaged image F shows the image of the physically suitable jig 1 attached to the distal edge of the thighbone B1 of the patient P on the operating table T and the distal edge of the thighbone B1, that is, the distal edge of the thighbone B1 in a state with the physically suitable jig 1 attached.

The configuration of the imaging apparatus 3 is described.

The imaging apparatus 3 is connected to the surgery assistance apparatus 2 through the I/F 206. The imaging apparatus 3 may have any well-known configuration and the detailed description is omitted. For example, the imaging apparatus 3 includes a central controller 301, an imager 302, a signal processor 303, and a communication controller 304.

The central controller 301 controls each unit of the imaging apparatus 3. Specifically, the illustration is omitted, and the CPU of the central controller 301 deploys the predetermined program read from the storage (not shown) in the work area of the memory (not shown), and the CPU performs the various processes according to the program.

Although illustration is omitted, for example, the imager 302 includes a lens unit including various lenses such as a zoom lens and a focus lens, an electronic imager which includes an image sensor such as a CCD (Charge Coupled Device) and CMOS (Complementary Metal-oxide Semiconductor) and which converts the optical image which passes various lenses of the lens unit to two-dimensional image signals, and an imaging controller which scans and drives the electronic imager with the timing generator and the driver. The imaging controller converts the optical image formed by the lens unit in a predetermined cycle to a two-dimensional image signal with the electronic imager, and reads out the frame image in a unit of one screen from the imaging region of the electronic imager and outputs the image to the signal processor 303.

For example, the signal processor 303 suitably adjusts the gain in each color component of the RGB for the signal of the analog value of the frame image transferred from the electronic imager, sample holds the data with a sample hold circuit (not shown) and converts the data to digital data with an A/D converter (not shown), performs a pixel interpolation process with a color process circuit (not shown) and a color processing process including a γcorrection process, and generates a brightness signal Y and color difference signals Cb, Cr (YUV data) in a digital value.

The communication controller 304 obtains the brightness signal Y and the color difference signals Cb, Cr (YUV data) of the frame image generated by the signal processor 303, and the obtained YUV data of the frame image (imaged image F) is transmitted to the surgery assistance apparatus 2.

Then, in the surgery assistance apparatus 2, the CPU of the central controller 201 performs the second obtaining process to obtain the image data (YUV data) of the digital value of the imaged image F received through the I/F 206 transmitted from the communication controller 304 of the imaging apparatus 3. The obtaining of the image data of the imaged image F can be performed sequentially each time the imaging of the imaged image F (generating of the YUV data of the frame image) is performed by the imaging apparatus 3 or can be performed at a timing desired by the user according to a predetermined operation on the operating unit 205 by the user.

The estimating program 203d is a program which executes the function regarding an estimating process which estimates the position and the posture of the physically suitable jig 1 in the imaged image F.

That is, the CPU of the central controller 201 reads out the estimating program 203d from the storage 203 and according to the estimating program 203d, performs the estimating process. Here, the CPU of the central controller 201 functions as the estimating unit in coordination with the estimating program 203d.

Specifically, the CPU of the central controller 201 recognizes the image recognizing unit 12 of the physically suitable jig 1 in the imaged image F obtained by the second obtaining process and estimates the position and the posture of the physically suitable jig 1 in the imaged image F based on the recognized result. That is, the CPU of the central controller 201 specifies the position and the posture of the marker 12a from the shape of the marker 12a (feature amount extracted from the marker 12a) of the image recognizing unit 12 in the imaged image F and estimates the position and the posture of the physically suitable jig 1 in the imaged image F from the specified result.

The method to recognize the image recognizing unit 12, that is, the method to specify the position and the posture of the marker 12a is a well-known technique, and the detailed description is omitted here.

The display control program 203e is a program to execute the function regarding the display control process which displays the augmented reality image overlapped with the imaged image F on the display 204 using the augmented reality (AR) technique.

That is, the CPU of the central controller 201 reads out the display control program 203e from the storage 203, and according to the display control program 203e, performs the display control process. Here, the CPU of the central controller 201 functions as the display controller in coordination with the display control program 203e.

Figure 5B:
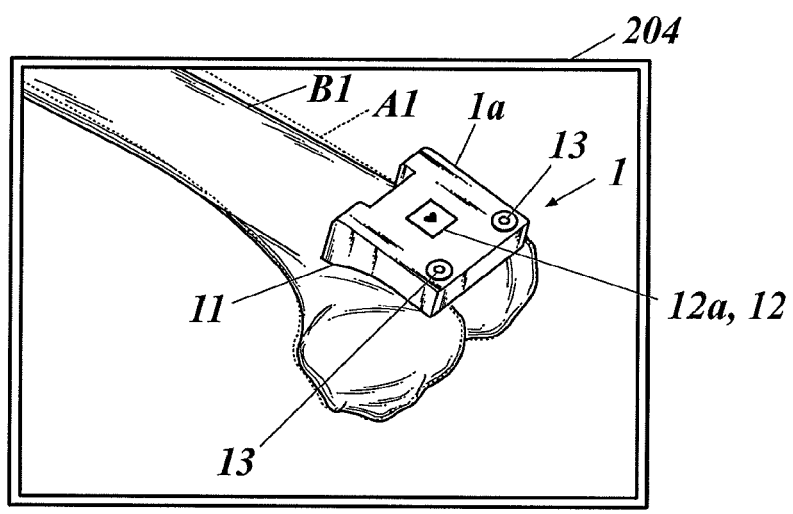
FIG. 5B is a diagram showing an example of an image displayed on a surgery assistance apparatus shown in FIG. 3.

Specifically, based on the reference image and the first jig information obtained by the first obtaining process, the CPU of the central controller 201 overlaps on the imaged image F a first augmented reality image A1 virtually showing the treated portion (thighbone B1) in the position and posture corresponding to the position and posture of the physically suitable jig 1 in the imaged image F estimated by the estimating process and displays the result on the display 204 (see FIG. 5B). More specifically, the first jig information includes the suitable attaching position and attaching direction of the physically suitable jig 1 on the three-dimensional model of the thighbone B1, that is, the first jig information includes the relative relation of the positions between the distal edge of the thighbone B1 and the physically suitable jig 1. Therefore, the CPU of the central controller 201 overlaps on the imaged image F the three-dimensional model of the distal edge of the thighbone B1 in the position and posture corresponding to the position and posture of the physically suitable jig 1 in the imaged image F estimated by the estimating process as the first augmented reality image A1 and displays the result on the display 204 (see FIG. 5B).

In FIG. 5B, only the outline of the three-dimensional model of the distal edge of the thighbone B1 is displayed with a broken line, but for example, the entire three-dimensional model of the distal edge of the thighbone B1 can be displayed in a translucent state.

When the relation of the positions between the thighbone B1 and the physically suitable jig 1 is adjusted, specifically, the attaching position and attaching direction of the physically suitable jig 1 with relation to the distal edge of the thighbone B1 is adjusted so as to match with the three-dimensional model of the distal edge of the thighbone B1 displayed as the first augmented reality image A1, the CPU of the central controller 201 overlaps on the imaged image F the second augmented reality image A2 virtually showing the attaching position and the attaching direction of the thighbone intramedullary rod inserted in the thighbone B1 to assist guiding of attaching the thighbone side member (not shown) with relation to the thighbone B1 based on the reference image, first jig information, and second jig information obtained by the first obtaining process, and the result is displayed on the display 204. More specifically, the second jig information includes the attaching position and attaching direction of various guiding assistance jigs such as the thighbone intramedullary rod and the thighbone osteotomy with the position of the physically suitable jig 1 on the three-dimensional model of the thighbone B1 as the reference, that is, the relative relation of the positions with relation to the physically suitable jig 1. Therefore, the CPU of the central controller 201 overlaps on the imaged image F the attaching position and attaching direction of the various guiding assistance jigs (for example, thighbone intramedullary rod) in the position and posture corresponding to the position and posture of the physically suitable jig 1 in the imaged image F estimated by the estimating process as the second augment reality image A2 and displays the result on the display 204 (see FIG. 5C).

Further, the CPU of the central controller 201 may overlap on the imaged image F the second augmented reality image A2 virtually showing the position and the direction of the osteotomy surface of the thighbone B1 with the thighbone intramedullary rod as the reference, and display the result on the display 204. The display of the second augmented reality image A2 showing the position and direction of the osteotomy surface of the thighbone B1 can be performed together with the display of the second augmented reality image A2 showing the attaching position and attaching direction of the intramedullary rod or can be performed at a different timing.

Figure 5C:
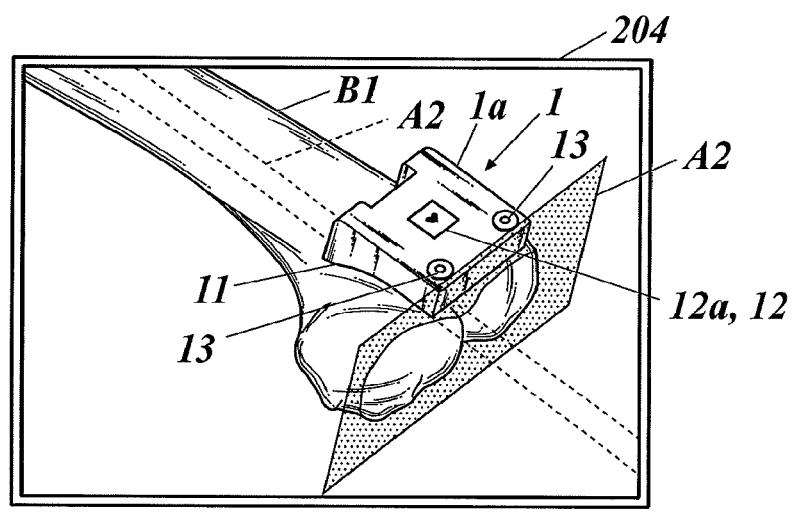
FIG. 5C is a diagram showing an example of an image displayed on the surgery assistance apparatus shown in FIG. 3.

FIG. 5C displays only the outline portion of the three-dimensional model of the thighbone intramedullary rod with broken lines. However, for example, the entire three-dimensional model of the thighbone intramedullary rod can be displayed in the translucent state. A planar shaped image is described as the second augmented reality image A2 showing the position and direction of the osteotomy surface of the thighbone B1, but this is one example and the image is not limited to the above. The shape and the dimensions can be suitably changed. Preferably, the second augmented reality image A2 is displayed in the translucent state. However, for example, this can be displayed in any state if the position and direction of the osteotomy surface of the thighbone B1 can be discriminated.

The contents of the process are substantially the same for the shinbone also, and the detailed description is omitted here. The CPU of the central controller 201 overlaps on the imaged image F the three-dimensional model of the proximal edge of the shinbone in the position and posture corresponding to the position and posture of the physically suitable jig in the imaged image F estimated by the estimating process as the first augmented reality image and displays the result on the display 204 (illustration omitted). Similarly, the CPU of the central controller 201 overlaps on the imaged image F the attaching position and attaching direction of the various guiding assistance jigs (for example, shinbone intramedullary rod) in the position and posture corresponding to the position and posture of the physically suitable jig in the imaged image F estimated in the estimating process as the second augmented reality image and displays the result on the display 204 (illustration omitted). Similarly, the CPU of the central controller 201 may overlap on the imaged image F the position and direction of the osteotomy surface of the shinbone with the position of the shinbone intramedullary rod as the reference as the second augmented reality image and display the result on the display 204.

In FIG. 5A to FIG. 5C, the illustration of the portions other than the thighbone B1 of the patient P is omitted. Actually, the tissues surrounding the thighbone B1 such as cartilage, tendon, ligament, skin, etc. are imaged by the imaging apparatus 3 and displayed on the display 204.

For example, the display 204 includes a LCD (Liquid Crystal Display) or an organic EL (Electro-Luminescence) display. The display 204 displays various screens according to the instruction of the display signal which is output from the CPU of the central controller 201 and input in the display 204 (see FIG. 5B and FIG. 5C).

The operating unit 205 includes a mouse or a keyboard provided with a data input key to input numerals and letters, cursor movement keys showing up, down, left, and right to select data or to move forward the screen, and various function keys. Then, the operating unit 205 outputs to the central controller 201 a predetermined operation signal according to the operation on the keyboard or mouse.

For example, the I/F 206 is connected to the imaging apparatus 3 to be able to communicate information through a wired cable (not shown) or a wireless communication network (for example, wireless LAN or Bluetooth (registered trademark)).

<Assistance Process>

The assistance process in the artificial knee joint replacement surgery is described with reference to FIG. 4, and FIG. 5A to FIG. 5C.

FIG. 4 is a flowchart showing an example of an operation regarding the assistance process used in the surgery assistance system 100. FIG. 5A is a diagram showing an example of the imaged image F imaged by the imaging apparatus 3, and FIG. 5B and FIG. 5C are diagrams showing an example of an image displayed on the operation assistance apparatus 2.

In the description below, the method to assist attaching the thighbone side member (implant) with relation to the thighbone B1 in performing the artificial knee joint replacement surgery is described, but substantially the same can be said for the shinbone side, and the detailed description is omitted.

As shown in FIG. 4, first, the CPU of the central controller 201 performs the preoperative planning process for the artificial knee joint replacement surgery (step S1).

Specifically, the CPU of the central controller 201 reads out and obtains tomographic image data I from the storage 203 according to a preoperative planning program 203a, generates image data of the reference image showing the three-dimensional form of the shinbone and the thighbone B1 of the patient P, and simulates and specifies the setting planned position of the thighbone side member included in the artificial knee joint on the three-dimensional model of the thighbone B1. The CPU of the central controller 201 simulates and generates the first jig information including the attaching position and attaching direction of the physically suitable jig 1 on the thighbone B1 on the three-dimensional model of the thighbone B1 and the second jig information including the attaching position and attaching direction of various guiding assistance jigs such as the thighbone intramedullary rod and the thighbone osteotomy guiding member to guide and assist attaching of the thighbone side member with relation to the thighbone B1. In the physically suitable jig 1, the CPU of the central controller 201 specifies the surface shape of the site fitting unit 11 including a complementary relation with the shape of the attaching position in the distal edge of the thighbone B1.

Next, the CPU of the central controller 201 obtains preoperative planning data D including the reference image showing the three-dimensional shape of the thighbone B1 of the patient P and the first jig information and the second jig information (step S2; First obtaining process).

Specifically, according to the first obtaining program 203b, the CPU of the central controller 201 reads out and obtains from the storage 203 the preoperative planning data D, and obtains the following, the image data of the reference image showing the three-dimensional shape of the thighbone B1 generated in the preoperative planning process, the first jig information including the attaching position of the physically suitable jig 1 attached to the distal edge of the thighbone B1 in the three-dimensional model of the thighbone B1, and the second jig information including the attaching position and attaching direction of the thighbone intramedullary rod to guide and assist the attaching of the thighbone side member with relation to the thighbone B1 on the three-dimensional model of the thighbone B1.

Then, when the three-dimensional printer is used, the main body unit 1a including the site fitting unit 11 including a surface shape having a complementary relation with the shape of the attaching position in the distal edge of the thighbone B1 is made as the member included in the physically suitable jig 1, and the physically suitable jig 1 is attached to the distal edge of the thighbone B1 (step S3). The physically suitable jig 1 is to be made and is to be attached to the distal edge of the thighbone B1 after the preoperative planning process (step S1), and for example, the above can be performed before the preoperative planning data D is obtained (step S2).

Then, the imaging apparatus 3 images the distal edge of the thighbone B1 in a state with the physically suitable jig 1 attached, and the CPU of the central controller 201 obtains the imaged image F imaged by the imaging apparatus (step S4).

For example, specifically, after the zoom magnification and the angle of view of the imaging apparatus 3 is adjusted to be able to image the distal edge of the thighbone B1 of the patient P on the operating table T, that is, the distal edge of the thighbone B1 with the physically suitable jig 1 attached, the distal edge of the thighbone B1 is sequentially imaged by the imaging apparatus 3. According to the second obtaining program 203c, the CPU of the central controller 201 sequentially obtains the image data of the imaged image F sequentially transmitted from the imaging apparatus 3 through the I/F 206.

Then, the CPU of the central controller 201 estimates the position and posture of the physically suitable jig 1 in the imaged image F (step S5; estimating process).

Specifically, according to the estimating program 203d, the CPU of the central controller 201 recognizes the image recognizing unit 12 of the physically suitable jig 1 in the imaged image F obtained by the second obtaining process, specifies the position and posture of the marker 12a from the shape of the marker 12a of the image recognizing unit 12 in the imaged image F, and estimates the position and posture of the physically suitable jig 1 in the imaged image F from the specified result.

Next, the CPU of the central controller 201 overlaps on the imaged image F the first augmented reality image A1 virtually showing the distal edge of the thighbone B1 using the augmented reality technique and displays the result on the display 204 (step S6; display control process).

Specifically, according to the display control program 203e, based on the reference image and the first jig information obtained by the first obtaining process, the CPU of the central controller 201 overlaps on the imaged image F the three-dimensional model of the distal edge of the thighbone B1 in the position and posture corresponding to the position and posture of the physically suitable jig 1 in the imaged image F estimated by the estimating process as the first augmented image A1 and displays the result on the display 204 (see FIG. 5B).

With this, the physician can confirm by sight the first augmented reality image A1, and understand the relation of the positions between the distal edge of the thighbone E1 and the physically suitable jig 1, that is, the displacement of the attaching position and the attaching direction of the physically suitable jig 1 with relation to the distal edge of the thighbone B1.

Then, the relation of the positions between the thighbone E1 and the physically suitable jig 1, specifically, the attaching position and attaching direction of the physically suitable jig 1 with relation to the distal edge of the thighbone B1 are adjusted to match the three-dimensional model of the distal edge of the thighbone 131 displayed as the first augmented reality image A1 by the physician and other staff (step S7).

Then, the CPU of the central controller 201 overlaps on the imaged image F the second augmented reality image A2 using the augmented reality technique to virtually show the attaching position and attaching direction of the thighbone intramedullary rod inserted in the thighbone B1 and displays the result on the display 204 (step S7; display control process).

For example, specifically, when the display of the second augmented reality image A2 is selected based on the predetermined operation on the operating unit 205 of the surgery assistance apparatus 2 by the physician, according to the display control program 203e, based on the reference image, the first jig information, and the second jig information obtained in the first obtaining process, the CPU of the central controller 201 overlaps on the imaged image F the attaching position and attaching direction of the thighbone intramedullary rod in the position and posture corresponding to the position and posture of the physically suitable jig 1 in the imaged image F estimated in the estimating process as the second augmented reality image A2 and displays the result on the display 204 (see FIG. 5C).

With this, the physician is able to confirm by sight the second augmented reality image A2 and understand the attaching position and attaching direction of the thighbone intramedullary rod with relation to the thighbone B1.

In the display control process in step S7, the CPU of the central controller 201 may overlap on the imaged image F the position and direction of the osteotomy surface of the thighbone B1 as the second augmented reality image A2 and displays the result on the display 204.

In this case, the physician confirms the second augmented reality image A2 by sight and is able to understand the position and direction of the osteotomy surface.

As described above, according to the surgery assistance system 100 of the present embodiment, it is possible to obtain the imaged image F which images the physically suitable jig 1 and treated portion (for example, thighbone B1, etc.) attached to the predetermined attached portion (for example, distal edge of the thighbone B1) on the body of the patient P who is treated with surgery. The surgery assistance system 100 of the present embodiment is also able to recognize the image recognizing unit 12 of the physically suitable jig 1 in the imaged image F and is able to estimate the position and the posture of the physically suitable jig 1 in the imaged image F. Then, based on the reference image in the three-dimensional shape showing the predetermined attached portion and treated portion in the body and the first jig information including the attaching position of the physically suitable jig 1 on the three-dimensional model based on the reference image, the first augmented reality image A1 virtually showing the treated portion in the position and posture corresponding to the position and posture of the physically suitable jig in the estimated imaged image F is overlapped on the imaged image F and the result is displayed on the display 204. Therefore, the physician is able to understand the displacement of the attaching position and attaching direction of the physically suitable jig 1 with relation to the attached portion by simply confirming by sight the first augmented reality image A1 displayed on the display 204. Therefore, the attaching position and the attaching direction of the physically suitable jig 1 with relation to the treated portion can be easily adjusted and the accuracy of attaching the physically suitable jig 1 can be enhanced. The physically suitable jig 1 does not always have to include a structure which guides and assists the guiding assistance jig such as the thighbone intramedullary rod. Therefore, for example, it is possible to provide a small physically suitable jig 1 that can be applied to minimally invasive surgery in which the width of cutting the skin can be relatively small.

Based on the second jig information including at least one of the direction and position of the guiding assistance jig (for example, thighbone intramedullary rod) which guides and assists attaching of the implant to the bone B (for example, thighbone B1) on the three-dimensional model based on the reference image, the second augmented reality image A2 virtually showing at least one of the direction and the position of the guiding assistance jig in the position and posture corresponding to the position and posture of the physically suitable jig 1 in the estimated imaged image F is overlapped on the imaged image F and the result is displayed on the display 204. Therefore, the physician is able to understand the attaching position and attaching direction of the guiding assistance jig with respect to the bone B by only confirming by sight the second augmented reality image A2 displayed on the display 204. As a result, the attaching of the implant can be performed more accurately.

The present invention is not limited to the above-described embodiments, and various modifications and changes in design can be made without leaving the scope of the present invention.

Below, a modification of the surgery assistance system 100 is described with reference to FIG. 6A and FIG. 6B.

According to the modification, the surgery assistance apparatus 2 overlaps on the imaged image F a third augmented reality image A3 which virtually shows at least one of the direction and the position of the cervical vertebra screw (implant) with the position and the posture corresponding to the position and the posture of the physically suitable jig in the imaged image F and displays the result on the display 204.

Figure 6A:
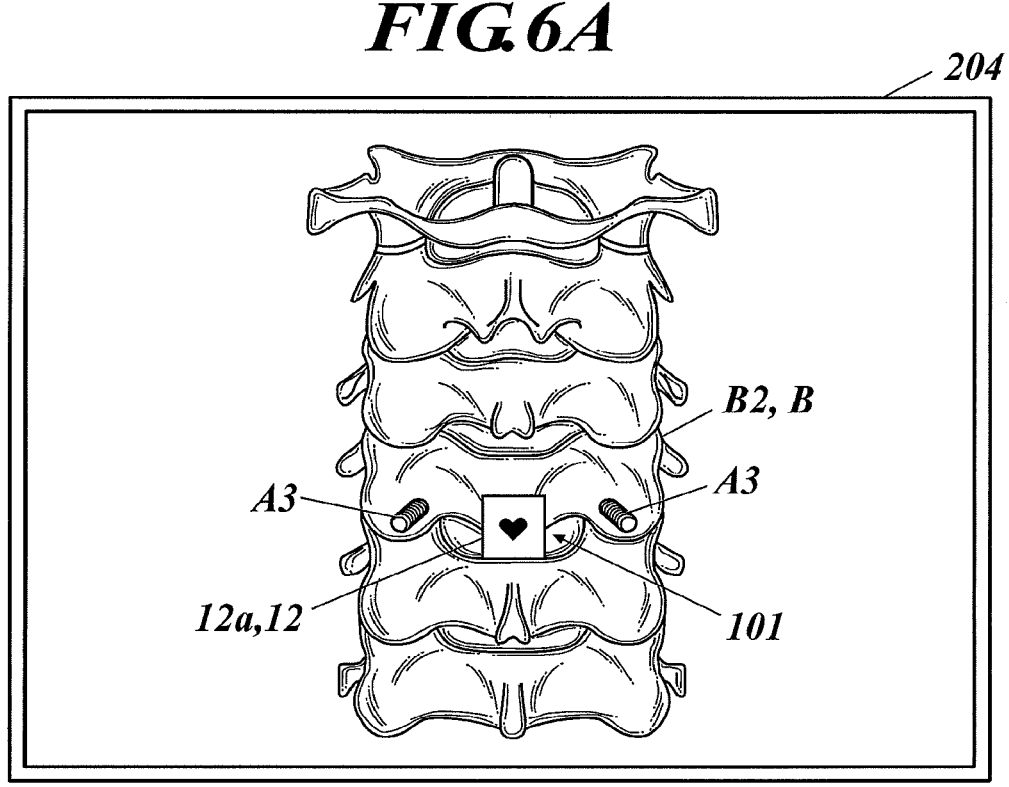
FIG. 6A is a rear view schematically showing a state in which a physically suitable jig is attached to a cervical vertebra.
Figure 6B:
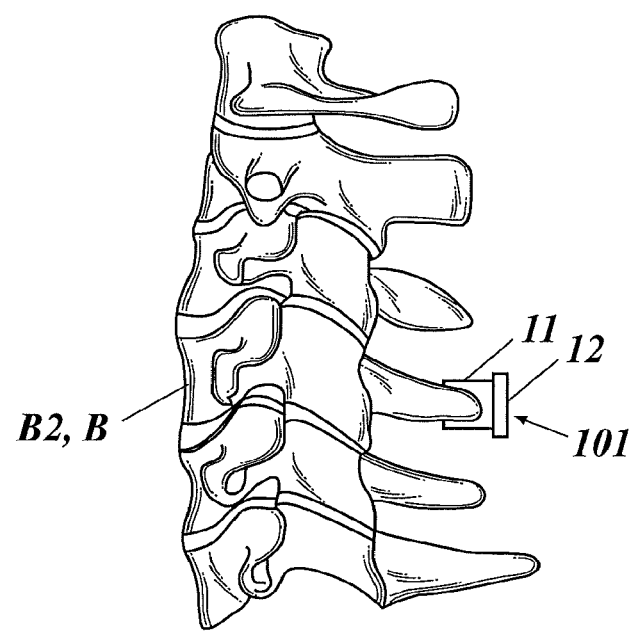
FIG. 6B is a side view schematically showing a state in which a physically suitable jig is attached to the cervical vertebra.

First, for example, the physically suitable jig 101 is attached to a predetermined position (for example, spinous process of fourth cervical vertebra) of the cervical vertebra B1 (see FIG. 6A and FIG. 6B). Substantially similar to the above-described embodiment, the physically suitable jig 101 includes a main body unit 1a formed with a site fitting unit 11 which can be fit in the predetermined position of the cervical vertebra B2 and the image recognizing unit 12 which includes a marker 12a so that the augmented reality image can be displayed by the surgery assistance apparatus 2.

Although illustration is omitted, the physically suitable jig 101 can be fixed in a state attached to the predetermined position of the cervical vertebra B2 using a pin or a biocompatible cement which can be removed.

The surgery assistance apparatus 2 performs the preoperative planning process to specify by simulation the shape and the dimensions of the cervical vertebra screw (not shown) to be attached and the attaching position and the attaching direction of the cervical vertebra screw with relation to the cervical vertebra. That is, the CPU of the central controller 201 establishes a coordinate system on a three-dimensional model of the cervical vertebra B2 displayed on the display 204, and simulates and specifies the implant information including the attaching position and the attaching direction of the cervical vertebra screw. The CPU of the central controller 201 simulates and generates the first jig information including the suitable attaching position and attaching direction of the physically suitable jig 100 with relation to the cervical vertebra B2 on the three-dimensional model of the thighbone B1 displayed on the display 204 based on the tomographic image data I.

Then, the CPU of the central controller 201 performs the first obtaining process to read and obtain the preoperative planning data D from the storage 203 and obtains the implant information including the attaching position and attaching direction of the cervical vertebra screw (implant) with relation to the cervical vertebra B2 on the three-dimensional model of the cervical vertebra B2.

Although the detailed description is omitted, the cervical vertebra screw is screwed in the cervical vertebra and is attached and fixed to the rod to fix the cervical vertebra.

The CPU of the central controller 201 overlaps on the imaged image F the third augmented reality image A3 virtually showing the attaching position and attaching direction of the cervical vertebra screw (not shown) with relation to the cervical vertebra B2 based on the reference image, the first jig information and the implant information obtained by the first obtaining process and displays the result on the display 204.

That is, with the physically suitable jig 101 attached to the cervical vertebra B2 (see FIG. 6A and FIG. 6B), the CPU of the central controller 201 recognizes the image recognizing unit 12 of the physically suitable jig 101 in the imaged image F imaged by the imaging apparatus 3, and estimates the position and the posture of the physically suitable jig 101 in the imaged image F based on the recognized result. Although illustration is omitted, based on the reference image and the first jig information obtained by the first obtaining process, the CPU of the central controller 201 overlaps on the imaged image F the first augmented reality image virtually showing the cervical vertebra B2 in the position and posture corresponding to the position and posture of the physically suitable jig 101 in the imaged image F estimated by the estimating process and displays the result on the display 204. Here, not only the fourth cervical vertebra as the treated portion but also other cervical vertebra such as the first to sixth cervical vertebra can be virtually shown in the displayed first augmented reality image.

Then, when the relation of the positions between the cervical vertebra B2 and the physically suitable jig 101, specifically, the attaching position and attaching direction of the physically suitable jig 101 with relation to the spinous process of the cervical vertebra B2 are adjusted to match with the three-dimensional model of the cervical vertebra B2 displayed as the first augmented reality image A1, based on the reference image, the first jig information and the implant information obtained in the first obtaining process, the CPU of the central controller 201 overlaps on the imaged image F the third augmented image A3 virtually showing the attaching position and attaching direction of the cervical vertebra screw with relation to the cervical vertebra B2 and displays the result on the display 204. Specifically, the implant information includes the attaching position and attaching direction of the implant such as the cervical vertebra screw with the position of the physically suitable jig 101 on the three-dimensional model of the cervical vertebra B2 as the reference, that is, the relative relation of the positions with relation to the physically suitable jig 101 is included. Therefore, the CPU of the central controller 201 overlaps on the imaged image F the attaching position and attaching direction of various implants (for example, cervical vertebra screw) in the position and the posture corresponding to the position and posture of the physically suitable jig 101 in the imaged image F estimated by the estimating process as the third augmented reality image A3, and displays the result on the display 204 (see FIG. 6A).

With this, the physician can confirm the third augmented reality image A3 by sight and can recognize the attaching position and attaching direction of the cervical vertebra screw with relation to the cervical vertebra B2.

Therefore, based on the implant information including at least one of the attaching direction and attaching position of the implant (for example, cervical vertebra screw) with relation to the bone B (for example, cervical vertebra B2) on the three-dimensional model based on the reference image, the third augmented reality image A3 virtually showing at least one of the direction and position of the implant in the position and posture corresponding to the position and posture of the physically suitable jig 1 in the estimated imaged image F is overlapped on the imaged image F and the result is displayed on the display 204. Therefore, the physician is able to understand the attaching position and attaching direction of the implant with relation to the bone B by only confirming by sight the third augmented reality image A3 displayed on the display 204. As a result, it is possible to attach the implant more accurately.

According to the above-described embodiment and the modification, for example, the artificial knee joint and the cervical vertebra screw are shown as examples of the implant, but these are merely examples, and the present invention is not limited to the above. For example, the above can be suitably changed to the spinal cage or vertebral centrum. The shape data of the implant can be made using a well-known CAD (Computer Aided Design) system and the shape data of the implant can be used in the preoperative planning process in the surgery assistance apparatus 2 or in the apparatus other than the surgery assistance apparatus 2.

Further, according to the above-described embodiment, the image virtually showing both the direction and the position of the jig such as the thighbone intramedullary rod is described as the second augmented reality image A2. However, this is merely one example and, the image may virtually show either one of the direction or position of the jig.

Similarly, according to the modification, the image virtually showing both the direction and position of the implant such as the cervical vertebra screw is described as the third augmented reality image A3. However, the above is merely one example, and the image may virtually show either one of the direction or the position of the implant.

According to the above-described embodiment and the modification, the bone B (for example, thighbone B or cervical vertebra B2) is described as the treated portion, but the treated portion may be soft tissue. Specifically, for example, a plurality of markers can be included in a deformable web-shaped material (such as a cloth), the deforming can be recognized, and the display of overlapping the augmented reality image can be performed according to the deforming. With this, the present invention can be applied to surgery of organs in which the shape changes, examples including the liver.

For example, the present invention can be applied to bone fracture surgery, and in this case, the physically suitable jig 1 is attached to one fractured bone piece and a first augmented reality image can be displayed virtually showing the other fractured bone piece to be connected with the one fractured bone piece as the treated portion.

Further, according to the above-described embodiment and the modification, the image recognizing unit 12 includes markers 12a and 12c, but these are merely examples. It is possible to suitably change whether the markers 12a and 12c are included. That is, even if a structure does not include markers, the image recognizing unit is to include features (for example, shape, color, etc.) that can be recognized and the position and posture of the physically suitable jigs 1, 101 in the imaged image F can be estimated.

The guiding unit to guide and assist attaching of the implant (not shown) can be provided detachably in the physically suitable jig 1 according to the present embodiment. Examples of the guiding unit include, guides which guide the inserting position and the inserting direction of the thighbone intramedullary rod (not shown) with relation to the thighbone B1 and guides which guide the osteotomy position of the thighbone B1.

When the guiding unit is able to come into contact with the surface of the thighbone B1, for example, preferably, similar to the site fitting unit 11, the guiding unit includes a contact surface with a surface shape in a complementary relation with the uneven shape of the surface of the distal edge of the thighbone 131 of the patient P.

The present invention is not limited to attaching the guiding unit to the physically suitable jig 1, and a guiding jig may be attached instead of the physically suitable jig 1 depending on the jig used in the surgery or the contents of the assistance. That is, for example, the physically suitable jig 1 can be detached in the state with the pin inserted through the pin inserting hole 13 and inserted in the thighbone B1. Then, the guiding jig can be attached with the position of the pin as the reference. By providing the image recognizing unit in the guiding jig, the surgery assistance apparatus 2 is able to recognize the image recognizing unit of the guiding jig in the imaged image F imaged by the imaging apparatus 3 and the desired augmented reality image can be displayed.

According to the above-described embodiment and the modification, a PC is shown as the surgery assistance apparatus 2, but this is merely one example, and the present invention is not limited to the above. For example, the surgery assistance apparatus may be a portable terminal such as a smartphone or tablet. When there is an imager in the portable terminal, the imager can be used instead of the imaging apparatus 3.

According to the surgery assistance apparatus 2 of the present embodiment, functions such as the first obtainer, the second obtainer, the estimating unit and the display controller can be performed by the CPU of the central controller 201 executing a predetermined program. Alternatively, a predetermined logic circuit can include a first obtaining section, a second obtaining section, an estimating section, and a display controlling section.

Further, as the computer-readable medium storing the program to execute the above-described processes, in addition to a ROM or a hard disk, a non-volatile memory such as a flash memory, or a portable storage medium such as a CD-ROM can be applied. A carrier wave can be applied as a medium to provide data of programs through a predetermined communication line.

The embodiments disclosed here are merely examples in all points, and do not limit the present invention. The scope of the present invention is shown by the scope of claims that follow and are not limited by the above description. The scope of the present invention includes the scope of claims and its equivalents, and any modifications made within the scope.

INDUSTRIAL APPLICABILITY

As described above, according to the present invention, the first augmented image A1 virtually showing the treated portion in the position and posture corresponding to the position and posture of the physically suitable jig 1 in the imaged image F can be overlapped with the imaged image F and the result can be displayed on the display 204. With this, the physician can confirm by sight the first augmented reality image A1 and can understand any shifts in the attaching position or attaching direction of the physically suitable jig 1 with relation to the attached portion.

Consequently, according to the present invention, when surgery is performed, it is possible to easily adjust the attaching position and attaching direction of the physically suitable jig 1 with relation to the treated portion, and the attaching accuracy of the physically suitable jig 1 can be enhanced. Further, the present invention can be preferably used in the technique which can provide a small physically suitable jig 1 which can be applied in minimally invasive surgery.

DESCRIPTION OF REFERENCE NUMERALS 100 surgery assistance system
1, 101 physically suitable jig
11 site fitting unit
12 image recognizing unit
12a, 12c marker
2 surgery assistance apparatus
201 central controller (first obtainer, second obtainer, estimating unit, display controller)
203 storage
204 display
3 imaging apparatus
A1 to A3 first to third augmented reality image
B bone
B1 thighbone
B2 cervical vertebra
F imaged image

What is claimed is:

1. A surgery assistance system comprising:
a physically suitable jig configured to be attached to a predetermined attached portion of a body on which surgery is performed, wherein the predetermined attached portion is a bone; and
a surgery assistance apparatus which displays an augmented reality image to support the surgery,
wherein
the physically suitable jig includes:
a site fitting unit which can be fitted in the predetermined attached portion which is the bone, and
an image recognized unit which includes a feature which can be image-recognized to display an augmented reality image with the surgery assistance apparatus,
the surgery assistance apparatus includes:
a first obtainer which obtains a reference image regarding a three-dimensional shape of the predetermined attached portion of the body and a treated portion which is the bone and on which the surgery is performed, and first jig information including an attaching position of the physically suitable jig in a three-dimensional model based on the reference image,
a second obtainer which obtains a captured image in which the physically suitable jig is attached to the predetermined attached portion and the treated portion which is the bone is imaged,
a central processing unit (CPU) configured to recognize the image recognized unit of the physically suitable jig in the captured image obtained by the second obtainer, and to estimate a position and posture of the physically suitable jig in the captured image, and a display controller which, based on the reference image and the first jig information obtained by the first obtainer, overlaps on the captured image of the bone which is the treated portion a first augmented reality image virtually showing the treated portion which is the bone in a position and a posture corresponding to the position and the posture of the physically suitable jig in the captured image estimated by the CPU and displays the overlapped image on a display.

2. The surgery assistance system according to claim 1, wherein the surgery includes attaching an implant to a bone as the treated portion, the first obtainer further obtains second jig information including at least one of a direction and a position of a guiding assistance jig which guides and assists attaching of the implant to the bone in the three-dimensional model based on the reference image, and based on the second jig information obtained by the first obtainer, the display controller overlaps on the captured image a second augmented reality image virtually showing at least one of a direction and a position of the guiding assistance jig in the position and the posture corresponding to the position and the posture of the physically suitable jig in the captured image estimated by the estimating unit and displays the overlapped image on the display.

3. The surgery assistance system according to claim 2, wherein the first obtainer further obtains implant information including at least one of a direction and a position to attach the implant to the bone in the three-dimensional model based on the reference image, and based on the implant information obtained by the first obtainer, the display controller overlaps on the captured image a third augmented reality image virtually showing at least one of the direction and the position of the implant in the position and the posture corresponding to the position and the posture of the physically suitable jig in the captured image estimated by the estimating unit and the above the overlapped image is displayed on the display.

4. The surgery assistance system according to claim 3, wherein, in the surgery assistance apparatus, the augmented reality image to be overlapped on the captured image and displayed by the display controller can be selected from the first to third augmented reality images.

5. The surgery assistance system according to claim 4, wherein the image recognized unit is formed separately from a main body of the physically suitable jig and the image recognized unit includes a marker fitted in a predetermined position of a surface of the main body of the physically suitable jig.

6. The surgery assistance system according to claim 4, wherein the image recognized unit is formed as one with the physically suitable jig in a predetermined position on a surface of the physically suitable jig.

7. The surgery assistance system according to claim 4, wherein the physically suitable jig includes a detachable guide that is configured to guide the physically suitable jig to a certain position or in a certain direction during the surgery.

8. The surgery assistance system according to claim 3, wherein the image recognized unit is formed separately from a main body of the physically suitable jig and the image recognized unit includes a marker fitted in a predetermined position of a surface of the main body of the physically suitable jig.

9. The surgery assistance system according to claim 3, wherein the image recognized unit is formed as one with the physically suitable jig in a predetermined position on a surface of the physically suitable jig.

10. The surgery assistance system according to claim 3, wherein the physically suitable jig includes a detachable guide that is configured to guide the physically suitable jig to a certain position or in a certain direction during the surgery.

11. The surgery assistance system according to claim 2, wherein the image recognized unit is formed separately from a main body of the physically suitable jig and the image recognized unit includes a marker fitted in a predetermined position of a surface of the main body of the physically suitable jig.

12. The surgery assistance system according to claim 2, wherein the image recognized unit is formed as one with the physically suitable jig in a predetermined position on a surface of the physically suitable jig.

13. The surgery assistance system according to claim 2, wherein the physically suitable jig includes a detachable guide that is configured to guide the physically suitable jig to a certain position or in a certain direction during the surgery.

14. The surgery assistance system according to claim 1, wherein the image recognized unit is formed separately from a main body of the physically suitable jig and the image recognized unit includes a marker fitted in a predetermined position of a surface of the main body of the physically suitable jig.

15. The surgery assistance system according to claim 1, wherein the image recognized unit is formed as one with the physically suitable jig in a predetermined position on a surface of the physically suitable jig.

16. The surgery assistance system according to claim 1, wherein the physically suitable jig includes a detachable guide that is configured to guide the physically suitable jig to a certain position or in a certain direction during the surgery.

* * * * *